(12) United States Patent
Yatsuyanagi et al.

(10) Patent No.: US 7,741,518 B2
(45) Date of Patent: Jun. 22, 2010

(54) METHOD FOR PRODUCING TRIFLUOROMETHANESULFONIC ANHYDRIDE

(75) Inventors: Hiroyuki Yatsuyanagi, Yurihonjo (JP); Hiroshi Koshiyama, Akita (JP); Tsunetoshi Honda, Akita (JP)

(73) Assignees: Mitsubishi Materials Corporation, Tokyo (JP); Jemco Inc., Akita-Ken (JP)

( * ) Notice: Subject to any disclaimer, the term of this patent is extended or adjusted under 35 U.S.C. 154(b) by 0 days.

(21) Appl. No.: 12/064,113

(22) PCT Filed: Oct. 24, 2006

(86) PCT No.: PCT/JP2006/321157

§ 371 (c)(1),
(2), (4) Date: Feb. 19, 2008

(87) PCT Pub. No.: WO2007/049613

PCT Pub. Date: May 3, 2007

(65) Prior Publication Data

US 2009/0118543 A1    May 7, 2009

(30) Foreign Application Priority Data

Oct. 25, 2005    (JP) .............................. 2005-310245

(51) Int. Cl.
*C07C 303/00* (2006.01)
(52) U.S. Cl. ...................................................... 562/872
(58) Field of Classification Search ................... 562/872
See application file for complete search history.

(56) References Cited

U.S. PATENT DOCUMENTS

| 5,004,829 A | 4/1991 | Aramaki et al. |
| 5,808,149 A | 9/1998 | Nakamura et al. |

FOREIGN PATENT DOCUMENTS

| JP | 2-268148 A | 11/1990 |
| JP | 9-227498 A | 9/1997 |
| JP | 10-114734 A | 5/1998 |
| JP | 11-236365 A | 8/1999 |
| JP | 11-236366 A | 8/1999 |

*Primary Examiner*—Jafar Parsa
(74) *Attorney, Agent, or Firm*—Leason Ellis LLP.

(57) ABSTRACT

This method for producing trifluoromethanesulfonic anhydride reacting trifluoromethanesulfonic acid with phosphorus pentoxide to produce trifluoromethanesulfonic anhydride, wherein hardening of the reaction solution due to polyphosphoric acid, which is produced as a byproduct, is prevented by using an excess amount of trifluoromethanesulfonic acid with respect to the phosphorus pentoxide.

4 Claims, No Drawings

METHOD FOR PRODUCING TRIFLUOROMETHANESULFONIC ANHYDRIDE

CROSS-REFERENCE TO PRIOR APPLICATION

This is a U.S. National Phase application under 35 U.S.C. §371 of International Patent Application No. PCT/JP2006/321157 filed Oct. 24, 2006, and claims the benefit of Japanese Patent Application No. 2005-310245 filed Oct. 25, 2005, both of which are incorporated by reference herein. The International Application was published in Japanese on May 3, 2007 as WO 2007/049613 A1 under PCT Article 21(2).

TECHNICAL FIELD

The present invention relates to a method for producing trifluoromethanesulfonic anhydride, which is useful as raw material for the synthesis of various functional materials including pharmaceuticals and agricultural chemicals.

This application claims priority from Japanese Patent Application No. 2005-310245 filed Oct. 25, 2005, the contents of which are incorporated herein by reference.

BACKGROUND ART

Conventionally, the method for producing trifluoromethanesulfonic anhydride by reacting trifluoromethanesulfonic acid with phosphorus pentoxide, as illustrated in the formula below, has been known (see Patent Documents 1 and 2). In this method, ordinarily an excess amount of phosphorus pentoxide (2 to 4 times mole) is used with respect to the trifluoromethanesulfonic acid in order to increase the conversion ratio of the trifluoromethanesulfonic acid.

$$6CF_3SO_3H + P_2O_5 \rightarrow 3(CF_3SO_2)_2O + 2H_3PO_4$$

This conventional production method, however, has the problem that when the reaction rate of the trifluoromethanesulfonic acid approaches approximately 60%, glass-like polyphosphoric acid produced as a byproduct accumulates and hardens the reaction solution, making it difficult to stir the reaction solution, and the reaction cannot be carried out further. It is also not easy to remove the byproduct of polyphosphoric acid or carry out processing after the reaction, and it is extremely difficult to distill and recover the unreacted trifluoromethanesulfonic acid and to dilute the polyphosphoric acid. For these reasons, the industrial production of trifluoromethanesulfonic anhydride has been plagued with problems.

In the conventional production method, since a large amount of unreacted trifluoromethanesulfonic acid remains, there is known the method of adding water or phosphoric acid, or adding further trifluoromethanesulfonate metal salt, to the distillation residue and then distilling this to recover the unreacted trifluoromethanesulfonic acid (see Patent Document 1). However, since the reaction between the solidified distillation residue and water is accompanied by a sudden rise in temperature due to the reaction heat, it is dangerous and difficult to perform industrially.

A method of using a fluorine-based solvent in order to improve the reduced yield due to hardening of the reaction solution is known (Patent Documents 3 and 4). Examples of the solvents that may be used in this method include fluoroalkylsulfonic anhydrides, fluoroalkylsulfonate esters, perfluoroalkanes, perfluroalkylamines, and perfluoropolyethers that contain the desired substance, but none of these solvents sufficiently dissolves polyphosphoric acid. As a result, after the reaction, it is necessary to add water or phosphoric acid as in the case of the conventional method in order to sufficiently recover the produced trifluoromethanesulfonic anhydride by distillation.

Another method that is known is that of producing trifluoromethanesulfonic anhydride by reacting with phosphorous pentachloride, phosphorous trichloride, and chlorine (Patent Documents 5 and 6). In this case, however, there is the problem that when, after the reaction, the produced trifluoromethanesulfonic anhydride is recovered by distillation, a byproduct of phosphorus oxychloride and the trifluoromethanesulfonic anhydride are difficult to separate because their boiling points are close to one another.

Patent Document 1: U.S. Pat. No. 5,004,829

Patent Document 2: Japanese Unexamined Patent Application, First Publication No. H02-268148

Patent Document 3: Japanese Unexamined Patent Application, First Publication No. H09-227498

Patent Document 4: Japanese Unexamined Patent Application, First Publication No. H10-114734

Patent Document 5: Japanese Unexamined Patent Application, First Publication No. H11-236365

Patent Document 6: Japanese Unexamined Patent Application, First Publication No. H11-236366

DISCLOSURE OF INVENTION

Problems to be Solved by the Invention

With regard to the method for producing trifluoromethanesulfonic anhydride in which trifluoromethanesulfonic acid is reacted with phosphorus pentoxide, the present invention solves the aforementioned problems of the conventional production methods, and provides a production method that prevents hardening of the reaction solution by the polyphosphoric acid that is produced as a byproduct and increases the reaction efficiency of the trifluoromethanesulfonic acid.

Means for Solving the Problems

The method for producing trifluoromethanesulfonic anhydride according to the invention includes: reacting trifluoromethanesulfonic acid with phosphorus pentoxide to produce trifluoromethanesulfonic anhydride, wherein hardening of the reaction solution due to polyphosphoric acid, which is produced as a byproduct, is prevented by using an excess amount of trifluoromethanesulfonic acid with respect to the phosphorus pentoxide.

An amount of the phosphorus pentoxide with respect to the trifluoromethanesulfonic acid in terms of mole ratio may be 0.3 or less.

An amount of the phosphorus pentoxide with respect to the trifluoromethanesulfonic acid in terms of mole ratio may be 0.05 to 0.2.

The method may further includes: distilling and recovering the produced trifluoromethanesulfonic anhydride, and then continuing distillation in order to distill and recover unreacted trifluoromethanesulfonic acid.

The method may further includes: distilling and recovering the produced trifluoromethanesulfonic anhydride under reduced pressure.

EFFECT OF THE INVENTION

In the production method of the invention, an excess amount of trifluoromethanesulfonic acid is used with respect to the phosphorus pentoxide; thereby, polyphosphoric acid that is produced as a byproduct is dissolved in the excess amount of trifluoromethanesulfonic acid. Thus, hardening of the reaction solution is prevented, and dehydration condensation reaction of the trifluoromethanesulfonic acid can proceed and ultimately it is possible to increase the reaction efficiency. The amount of phosphorus pentoxide with respect to trifluoromethanesulfonic acid in terms of mole ratio is preferably 0.3 or less, and more preferably 0.05 to 0.2.

Further, because the reaction solution does not harden, when the unreacted trifluoromethanesulfonic acid is recovered from the distillation residue, one has only to continue the distillation. It is not necessary to add phosphoric acid or trifluoromethanesulfonate metal salt, for example, to the distillation residue, as was performed conventionally, and the unreacted trifluoromethanesulfonic acid can be recovered effectively.

BEST MODE FOR CARRYING OUT THE INVENTION

The method for producing trifluoromethanesulfonic anhydride according to the invention involves the use of excess amount of trifluoromethanesulfonic acid with respect to the phosphorus pentoxide when reacting trifluoromethanesulfonic acid with phosphorus pentoxide to produce trifluoromethanesulfonic anhydride. This prevents hardening of the reaction solution due to the polyphosphoric acid that is produced as a byproduct.

When trifluoromethanesulfonic acid is reacted with phosphorus pentoxide to produce trifluoromethanesulfonic anhydride, the conventional method uses an excess amount (2 to 4 times mole) of phosphorus pentoxide with respect to the trifluoromethanesulfonic acid in order to increase the reaction rate of the trifluoromethanesulfonic acid. In contrast, the production method of the present invention is the exact opposite of the convention production method, and uses an excess amount of trifluoromethanesulfonic acid with respect to the phosphorus pentoxide.

By using an excess amount of trifluoromethanesulfonic acid with respect to the phosphorus pentoxide, the byproduct of polyphosphoric acid is dissolved by the excess amount of trifluoromethanesulfonic acid; thereby, a homogeneous reaction system can be maintained without hardening the reaction solution. As a result, dehydration condensation reaction of the trifluoromethanesulfonic acid progresses adequately and it is eventually possible to efficiently produce trifluoromethanesulfonic anhydride. Further, the unreacted trifluoromethanesulfonic acid can be recovered easily by continuing distillation.

Specifically, in terms of the mole ratio of phosphorus pentoxide to trifluoromethanesulfonic acid, the amount of phosphorus pentoxide that is used is preferably 0.3 or less, and more preferably 0.05 to 0.2. If the phosphorus pentoxide is used at a mole ratio of greater than 0.3 with respect to trifluoromethanesulfonic acid, the polyphosphoric acid that is produced as a byproduct cannot be sufficiently dissolved, and the polyphosphoric acid gradually accumulates and hardens the reaction solution. On the other hand, if the phosphorus pentoxide is used at a mole ratio of less than 0.05 with respect to trifluoromethanesulfonic acid, a production amount of trifluoromethanesulfonic anhydride becomes small, and this is not preferable. To carry out industrial production, the amount of phosphorus pentoxide that is used is preferably even higher than the amount described above.

The trifluoromethanesulfonic anhydride that is produced by the dehydration condensation reaction of the trifluoromethanesulfonic acid can be recovered from the reaction system by distillation. Conventionally, it has been known that in the case where the distillation temperature is high when recovering trifluoromethanesulfonic anhydride by distillation in the presence of trifluoromethanesulfonic acid, the produced trifluoromethanesulfonic anhydride undergoes the following side reaction with the trifluoromethanesulfonic acid.

Distillation is possible at normal pressure, but in order to inhibit this side reaction, it is more preferable for distillation to be carried out at reduced pressure and at the lowest possible temperature. Specifically, it is preferable for the internal temperature during distillation to be kept as low as possible within a range of 30° C. to 90° C., and to this end, the distillation is preferably carried out at an internal pressure of 500 torr or less, particularly within the range of 300 to 30 torr. For example, by recovering the distillate at an internal pressure of 90 torr and an internal temperature up to 90° C., it is possible to obtain highly pure trifluoromethanesulfonic anhydride.

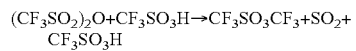
$(CF_3SO_2)_2O + CF_3SO_3H \rightarrow CF_3SO_3CF_3 + SO_2 + CF_3SO_3H$ The unreacted trifluoromethanesulfonic acid can also be readily recovered by continuing the distillation. As the distillation conditions when recovering the trifluoromethanesulfonic acid by distillation, an internal pressure is preferably 100 torr or less, and more preferably 50 torr or less. The internal temperature depends on the degree of vacuum, but it is preferably 200° C. or less. As a specific example, after recovering the trifluoromethanesulfonic anhydride by reduced-pressure distillation, the distillate is switched and distillation is continued at an internal pressure of 10 torr and an internal temperature up to about 200° C.; thereby, it is possible to efficiently recover the excess amount of unreacted trifluoromethanesulfonic acid that has not contributed to the reaction.

EXAMPLES

Examples of the present invention are described below along with comparative examples.

Example 1

450 g (3.0 mol) of trifluoromethanesulfonic acid was introduced into a reaction vessel provided with a thermometer, a reflux condenser, and stirring vanes, and then 85.2 g (0.60 mol) of phosphorus pentoxide was added. These were reacted for 18 hours at room temperature while stirring. Immediately after adding the phosphorus pentoxide, the reaction system was a dispersion system (the phosphorus pentoxide powder was dispersed within the solution), but at about 8 hours the solution became homogeneous.

Next, the internal pressure was reduced to 90 torr and the distillate up to an internal temperature of 90° C. was recovered; thereby, trifluoromethanesulfonic anhydride was obtained. The amount of the recovered trifluoromethanesulfonic anhydride was 185.5 g, and the purity was 99% determined by the gas chromatography. The yield of the produced anhydride with respect to the amount of the introduced trifluoromethanesulfonic acid was 43%.

Distillation was continued at an internal pressure of 10 torr and an internal temperature up to about 200° C.; thereby, 247.2 g of unreacted trifluoromethanesulfonic acid was recovered. The recovery rate with respect to the introduced trifluoromethanesulfonic acid was 55%. The reaction yield of the trifluoromethanesulfonic anhydride was calculated from the amount of consumed trifluoromethanesulfonic acid ((introduced amount)−(recovered amount)), and was 96%.

Example 2

As in Example 1, 9 kg (60 mol) of trifluoromethanesulfonic acid was introduced and then 1.7 kg (12 mol) of phosphorus pentoxide was added. This was reacted for 18 hours at room temperature.

The trifluoromethanesulfonic anhydride was recovered through reduced-pressure distillation, and then reduced-pressure distillation was continued in order to recover the trifluoromethanesulfonic acid. The amount of obtained trifluoromethanesulfonic anhydride was 3.64 kg, and the yield of the produced trifluoromethanesulfonic anhydride with respect to the amount of the introduced trifluoromethanesulfonic acid was 43%. The amount of recovered unreacted trifluoromethanesulfonic acid was 4.98 kg. The reaction yield of the trifluoromethanesulfonic anhydride was calculated from the amount of consumed trifluoromethanesulfonic acid ((introduced amount)−(recovered amount)), and was 95%.

Example 3

Trifluoromethanesulfonic anhydride was produced and the unreacted trifluoromethanesulfonic acid was recovered in the same manner as in Example 1, except that the amount of introduced trifluoromethanesulfonic acid and the amount of phosphorus pentoxide added was adjusted as shown in Table 1. The results are shown in Table 1.

TABLE 1

| No. | TfOH | $P_2O_5$ | $P_2O_5$/TfOH | TfOH anhydride | Purity | Recovered TfOH | Reaction yield |
|---|---|---|---|---|---|---|---|
| 1 | 450 g (3.0 mol) | 85.2 g (0.6 mol) | mol ratio of 0.2 | 185.5 g (43.4%) | 99% | 247.2 g (54.9%) | 96% |
| 2 | 9 kg (60 mol) | 1.7 kg (12 mol) | mol ratio of 0.2 | 3.63 kg (42.5%) | 99% | 4.98 kg (55.3%) | 95% |
| 3 | 450 g (3.0 mol) | 21.3 g (0.15 mol) | mol ratio of 0.05 | 51.2 g (12.0%) | 99% | 393.8 g (87.5%) | 96% |
| 4 | 720 g (4.8 mol) | 818 g (5.76 mol) | mol ratio of 1.2 | 448.0 g (64.9%) | 98% | 15.0 g (2.1%) | 66% |
| 5 | 450 g (3.0 mol) | 0.43 g (0.003 mol) | mol ratio of 0.001 | 1.0 g (0.20%) | 98% | 440 g (98.0%) | 10% |

(Note) No. 1 through 3 are Examples, and No. 4 and 5 are Comparative Examples.

TfOH is trifluoromethanesulfonic acid.

Comparative Examples 1 and 2

Trifluoromethanesulfonic anhydride was produced and the unreacted trifluoromethanesulfonic acid was recovered in the same manner as in Example 1, except that the amount of introduced trifluoromethanesulfonic acid and the amount of added phosphorus pentoxide was adjusted as shown in Table 1. The results are shown in Table 1.

INDUSTRIAL APPLICABILITY

In accordance with the present invention, in the process of producing trifluoromethanesulfonic anhydride, which is useful as raw material for the synthesis of various functional materials including pharmaceuticals and agricultural chemicals, it is possible to increase the reaction efficiency and also to effectively recover unreacted trifluoromethanesulfonic acid. Therefore, the present invention can be favorably adopted in the process for producing trifluoromethanesulfonic anhydride.

The invention claimed is:

1. A method for producing trifluoromethanesulfonic anhydride, comprising:

reacting trifluoromethanesulfonic acid with phosphorus pentoxide to produce trifluoromethanesulfonic anhydride, wherein an amount of the phosphorus pentoxide with respect to the trifluoromethanesulfonic acid in terms of mole ratio is 0.3 or less, thereby, hardening of the reaction solution due to polyphosphoric acid, which is produced as a byproduct, is prevented.

2. The method for producing trifluoromethanesulfonic anhydride according to claim 1, wherein an amount of the phosphorus pentoxide with respect to the trifluoromethanesulfonic acid in terms of mole ratio is 0.05 to 0.2.

3. The method for producing trifluoromethanesulfonic anhydride according to claim 1, wherein the method further comprises:

distilling and recovering the produced trifluoromethanesulfonic anhydride, and then continuing distillation in a state where phosphoric acid or trifluoromethanesulfonate metal salt is not newly added, in order to distill and recover unreacted trifluoromethanesulfonic acid.

4. The method for producing trifluoromethanesulfonic anhydride according to claim 1, wherein the method further comprises:

distilling and recovering the produced trifluoromethanesulfonic anhydride under reduced pressure.

* * * * *